(12) United States Patent
Laubert et al.

(10) Patent No.: US 8,262,670 B2
(45) Date of Patent: Sep. 11, 2012

(54) SELF-RETAINING SURGICAL DRIVER

(75) Inventors: Nikolay S. Laubert, Allentown, PA (US); Matthew E. Kohler, East Greenville, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 288 days.

(21) Appl. No.: 12/607,451

(22) Filed: Oct. 28, 2009

(65) Prior Publication Data
US 2011/0098715 A1   Apr. 28, 2011

(51) Int. Cl.
*A61B 17/58* (2006.01)
*B25B 15/00* (2006.01)
(52) U.S. Cl. ............ 606/104; 81/448; 81/460; 81/461
(58) Field of Classification Search .............. 606/104, 606/314; 81/443, 447, 451–456, 448, 460, 81/461
See application file for complete search history.

(56) References Cited

U.S. PATENT DOCUMENTS

| 3,288,184 A * | 11/1966 | Kyser ................................ 81/443 |
| 4,779,494 A | 10/1988 | Quach |
| 5,355,752 A * | 10/1994 | Keenan et al. ................... 81/453 |
| 6,973,860 B2 | 12/2005 | Nish |
| 6,997,086 B1 * | 2/2006 | Graham ............................ 81/451 |

* cited by examiner

*Primary Examiner* — Kevin T Truong
*Assistant Examiner* — Diana S Jones
(74) *Attorney, Agent, or Firm* — RatnerPrestia

(57) ABSTRACT

A surgical tool includes a proximal end, a distal end and a longitudinal axis extending from the proximal end to the distal end. The surgical tool has a fastener engagement tip having a spring extension extending substantially parallel to the longitudinal axis of the surgical tool. The spring extension is resiliently flexible and deflectable between a first arrangement, in which the spring extension is in a relaxed state, and a second arrangement, in which the spring extension is deflected to facilitate insertion of the fastener engagement tip into a fastener slot.

16 Claims, 6 Drawing Sheets

SELF-RETAINING SURGICAL DRIVER

FIELD OF THE INVENTION

The present invention relates generally to surgical instruments, and more specifically to a surgical instrument having an engagement tip that engages an implant component under a stored energy to retain the component on the tip.

BACKGROUND OF THE INVENTION

Surgical implants commonly utilize one or more types of fasteners to secure the implants in a desired position in the body of a human or animal. Many implants utilize bone screws, bone nails or anchoring blades to anchor the implants to bone, for example. Bone screws can be anchored to bone by driving the bone screws into holes prepared in the bone using a screw driver designed for surgical applications.

Implant components, such as bone fasteners and bone plates, can be very small, making it difficult to handle them during surgery. It is important that these components be securely attached to instruments during insertion, so that they do not detach from the insertion instrument and drop into an incision. Because of their is sharp features, many components present a serious risk of internal injury if dropped into an incision. Moreover, it can be very difficult to retrieve implant components that are dropped in an incision, due to their relatively small size. Retrieval of a dropped implant component can result in delay and complications in a surgical procedure.

SUMMARY OF THE INVENTION

The present invention offers mechanisms for securely handling surgical implant components as they are being inserted during surgical procedures. In a first embodiment, a surgical tool includes a proximal end, a distal end and a longitudinal axis extending from the proximal end to the distal end. The surgical tool has an engagement tip having at least one spring extension extending in a direction substantially parallel to the longitudinal axis of the surgical tool. The at least one spring extension is resiliently flexible and deflectable between a first arrangement, in which it is in a relaxed state, and a second arrangement, in which it is deflected.

A surgical tool in accordance with another embodiment of the invention includes a proximal end, a distal end and a longitudinal axis extending from the proximal end to the distal end. The surgical tool has an engagement tip having at least one spring extension extending substantially parallel to the longitudinal axis of is the surgical tool. The at least one spring extension is resiliently flexible and deflectable between a first arrangement, in which it is in a relaxed state, and a second arrangement, in which it is deflected toward the longitudinal axis of the surgical tool.

A surgical tool in accordance with another embodiment of the invention includes a proximal end, a distal end and a longitudinal axis extending from the proximal end to the distal end, the surgical tool comprising an engagement tip having at least one spring extension extending substantially parallel to the longitudinal axis of the surgical tool. The at least one spring extension is resiliently flexible and deflectable between a first arrangement, in which it is in a relaxed state, and a second arrangement, in which it is deflected into a condition under a stored energy. The stored energy biases the at least one spring extension toward the first arrangement.

BRIEF DESCRIPTION OF THE DRAWINGS

The foregoing summary and the following detailed description will be better understood in conjunction with the drawing figures, of which.

DETAILED DESCRIPTION OF THE PREFERRED EMBODIMENTS OF THE INVENTION

Figure 1:
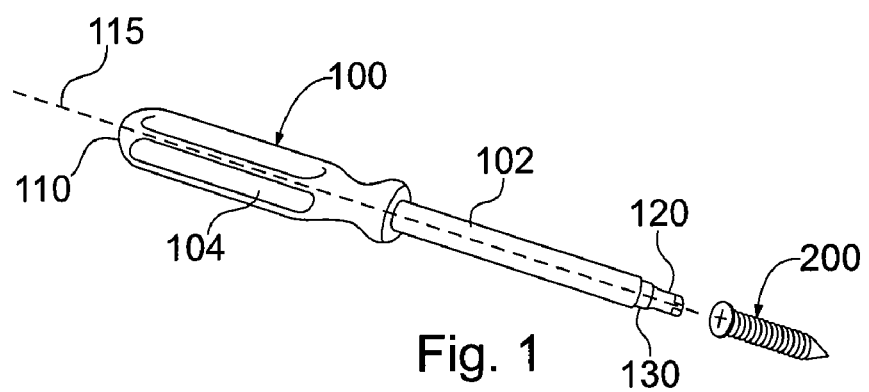
FIG. 1 is a perspective view of a surgical tool in accordance with one embodiment of the invention, the surgical tool being shown with a fastener.

Although the invention is illustrated and described herein with reference to specific embodiments, the invention is not intended to be limited to the details shown. Rather, various modifications may be made in the details within the scope and range of equivalents of the claims and without departing from the invention.

The present invention addresses a number of challenges encountered in surgical procedures. Specifically, the present invention addresses some conflicting interests encountered in the handling of small surgical implant components, including but not limited to fasteners used to anchor implants. On one hand, fasteners need to be securely attached to drivers or other insertion tools, so as to prevent the fasteners from separating from the tools as they are inserted. On the other hand, the insertion tool must be able to detach from the fastener after the fastener is anchored in place, and easily detach from the fastener with little required effort. It is desirable to use a tool that accommodates existing fastener configurations, rather than require a customized fastener configuration to accommodate the new tool.

Some tools used in unrelated applications are made of magnetic materials that hold metal fasteners under magnetic force. The magnetic force is strong enough to keep the fastener on the end of the tool, but weak enough so that a user can easily separate the tool from the fastener after the fastener is anchored into a material. Magnetic tools accommodate conventional metal fasteners, so that special fastener designs are not needed. Unfortunately, magnetic tools offer no benefit to is surgeons who handle surgical implant fasteners, because the implant fasteners are often made of non-magnetic material, such as titanium or titanium alloys.

The present invention provides surgical tools that securely attach to surgical fasteners during insertion. Tools in accordance with the invention do not require any changes to existing implant fasteners, although the tools can work with modified or customized fastener configuration if desired. Instead, the tools incorporate a mechanism for enhancing the engagement with existing fastener types. Tools in accordance with the invention provide enhanced engagement with many existing types of fasteners, including but not limited to bone screws and bone nails. For purposes of this description, the present invention will be described as it would be embodied in a surgical screw driver for driving bone screws. It will be appreciated from the examples described herein that that the present invention can be embodied in any conventional screw driver configuration, including but not limited to a Philips head, slotted (or "flat") head, square head, hexagonal head, hexalobular (or "star") head, or spline head, to name a few examples. It will be further appreciated that the present invention need not be embodied in surgical screw drivers, but can be embodied in other types of surgical tools, including but not limited to tools for inserting, advancing or manipulating prosthetic implants, artificial disc implants, bone plates, and other implant components.

Drivers in accordance with the invention can utilize a fastener engagement tip having a built-in mechanism for retaining fasteners. The retaining mechanism requires no action or step by the surgeon to operate it, other than the normal steps the surgeon would employ when using a screw driver. The retaining mechanism is engaged and disengaged in the course of using the screw driver as it would normally be used.

Retaining mechanisms in accordance with the present invention can utilize components that move between a disengaged position, which the mechanism assumes prior to connecting the tool to the fastener, and an engaged position, which the mechanism assumes when the tool is inserted into the fastener. The moving components of the retaining mechanism can move within the confines of conventional screw driver slots, such as Philips head slots, slotted (or "flat") head is slots, square head slots, hexagonal head slots, hexalobular (or "star") head slots, or spline head slots, to name a few examples. As such, the retaining mechanism accommodates existing bone screw heads.

Surgical tools in accordance with the invention may include a proximal end, a distal end and a longitudinal axis extending from the proximal end to the distal end. The surgical tool may also include a fastener engagement tip, as noted above, having one or more spring extensions. Spring extensions may extend substantially parallel to one another in a direction substantially parallel to the longitudinal axis of the surgical tool. Spring extensions may also be resiliently flexible and deflectable between a first arrangement, in which the spring extensions are in a relaxed state, and a second arrangement, in which at least one of the spring extensions is deflected toward another of the spring extensions. In the second arrangement, one of the spring extensions may be deflected toward the longitudinal axis of the tool. Moreover, one of spring extensions may be deflected into a condition under stored energy when in the second arrangement. In such a case, the stored energy biases that spring extension toward the first arrangement.

Figure 2:
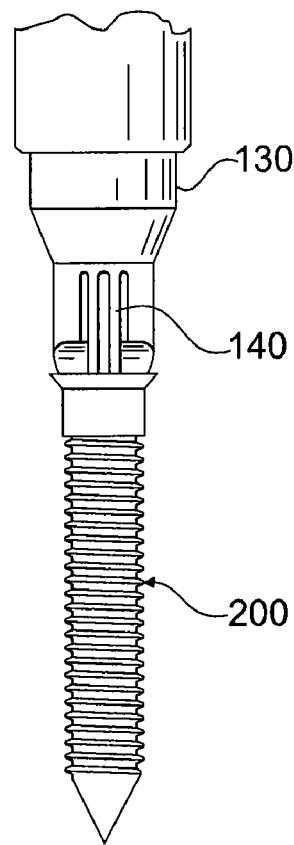
FIG. 2 is an enlarged perspective view of the surgical tool of FIG. 1, truncated for clarity, showing the tool in engagement with a bone fastener.

Referring to FIGS. 1 and 2, a surgical driver instrument or "driver" 100 is shown in accordance with one embodiment of the invention. Driver 100 includes a proximal end 110, a distal end 120 and a longitudinal axis 115 extending from the proximal end to the distal end. A fastener engagement tip 130 extends generally parallel to axis 115. Fastener engagement tip 130 is designed to engage and retain a fastener on distal end 120. More specifically, fastener engagement tip 130 includes a retaining mechanism 140 for securing a fastener on the driver with an enhanced engagement. FIG. 2 shows driver 100 engaged to a Philips head titanium bone screw 200.

Figure 3:
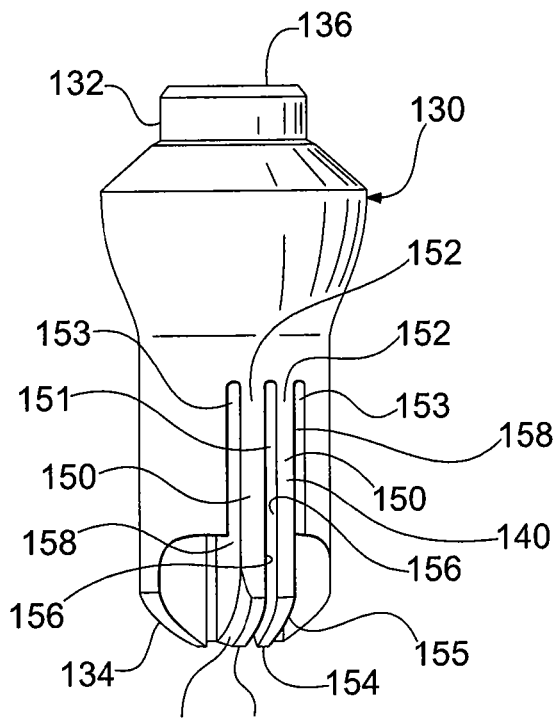
FIG. 3 is a perspective view of a fastener engagement tip used on the surgical tool in FIG. 1.
Figure 4:
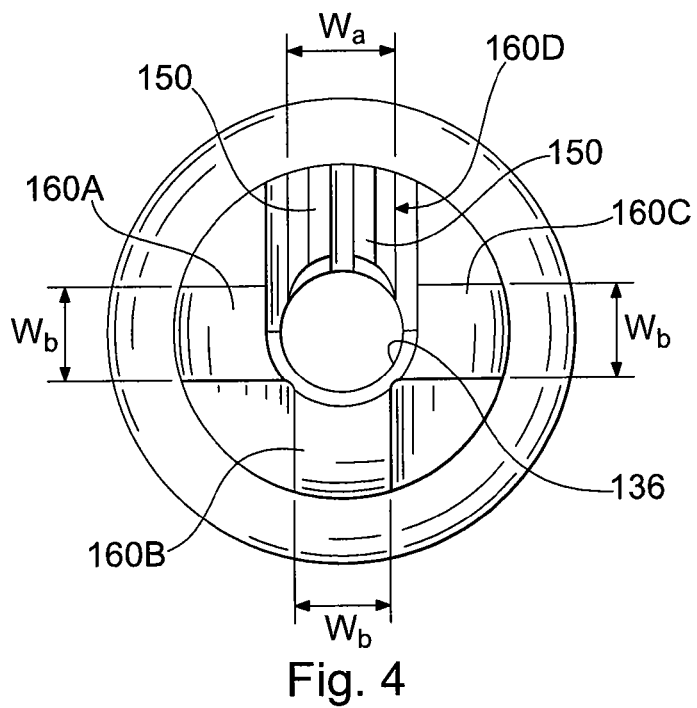
FIG. 4 is an end view of the fastener engagement tip of FIG. 3.

Referring now to FIGS. 3 and 4, retaining mechanism 140 is built into fastener engagement tip 130. Fastener engagement tip 130 assumes the general shape and form of a Philips head screw driver tip that can be used with conventional titanium bone screws. Retaining mechanism 140 includes two spring extensions 150 extending substantially parallel to one another. Spring extensions 150 are formed of a resilient flexible material, such as Titanium, that allows the extensions to bend or deflect in response to force, and return to their original configuration upon removal of force. Spring extensions 150 may be integrally formed with the rest of fastener engagement tip 130. The phrase "integrally formed", as used herein, refers to elements that are formed as one single unitary body, as opposed to elements that are joined elements by welding or other mechanical connections.

Spring extensions in accordance with the invention are deflectable between a first arrangement, in which the spring extensions are in a relaxed state, and a second arrangement, in which the spring extensions are deflected. Depending on the configuration, one or more of the spring extensions may be deflected toward other spring extensions in the fastener engagement tip. One or more spring extensions may also be deflected toward the longitudinal axis of the driver. In the second arrangement, one or more of the spring extensions may be deflected under a stored energy sufficient to return the deflected spring extensions to their original respective positions in the first arrangement.

Fastener engagement tips in accordance with the invention may be integrally formed with other sections of the surgical tool. Alternatively, fastener engagement tips in accordance with the invention may be separate components that are attached to other sections of a tool during manufacturing. Referring to FIGS. 1 and 3, for example, fastener engagement tip 130 is a separate component that is joined to a shank 102. Shank 102 is joined to a handle 104. Handle 104, shank 102 and fastener engagement tip 130 may be joined to one another using any suitable connection method or means. Fastener engagement tip 130 includes a generally cylindrical proximal coupling end 132 and a distal fastener engagement end 134.

Fastener engagement tips in accordance with the invention may be connected to shanks or other tool sections either permanently, or with a detachable connection. Where detachable connections are used, a number of connection methods may be used, including but not limited to a friction connection and/or a magnetic connection, the latter being suitable even if the fasteners and surgical implant are formed of non-materials.

Fastener engagement tip 130 assumes the general shape and form of a Philips head screw driver tip, as noted above, but with part of the tip formed by spring extensions 150. Tip 130 includes four blades 160A, 160B, 160C and 160D, with blade 160D comprising the two spring elements 150. It will be appreciated that fastener engagement tips of the present invention can feature a Philips head tip with spring extensions in more than one blade. For example, the Philips head tip may include two blades having spring extensions, three blades having spring extensions, or all four blades having spring extensions. Incorporating spring extensions into a greater number of blades can increase the amount of retaining force on the bone screw, and distribute retaining force over a larger area of the screw head.

Each spring extension 150 forms a cantilever member, with one end 152 joined at a middle portion of fastener engagement tip 130, and the opposite end 154 being a free end. Each extension 150 also has an inner face 156 and an outer face 158 opposite the inner face. Spring extensions 150 are separated from one another by an inner slit 151 that is centrally located between the spring extensions. Inner slit 151 separates inner faces 156 from one another. A pair of outer slits 153 extend adjacently to outer faces 158. In this arrangement, spring extensions 150 are bendable about joined ends 152 and toward one another. As noted above, spring extensions 150 collectively form blade 160D, forming part of the Philips head configuration. As such, spring extensions 150 are configured for insertion into a Philips head slot on the head of a bone screw, along with blades 160A-160C.

The width "$W_a$" of blade 160D (i.e. the combined width of spring extensions 150 and inner slit 151) is variable, depending on whether the spring extensions are positioned in the first arrangement (relaxed state) or the second arrangement (deflected state). In contrast, the individual widths "$W_b$" of the three solid blades 160A-160C are fixed. When spring extensions 150 are in the relaxed state, their width "$W_a$" is greater than the fixed width "$W_b$" of the other three blades. Width "$W_a$" is also configured to be greater than the width of Philips head slots on bone screws when spring extensions 150 are in the relaxed state. Width "$W_a$" is less than the width of Philips head slots on bone screws when spring extensions 150 are compressed together in the second arrangement.

Each spring extension 150 has a chamfered or beveled edge 155 connecting the free end 154 of the spring extension with the outer face 158 of that spring extension. Beveled edges 155 form lead-in edges on the outside of blade 160D. The lead-in edges collectively form a tapered tip to facilitate insertion of the blade into a is screw slot.

Figure 11:
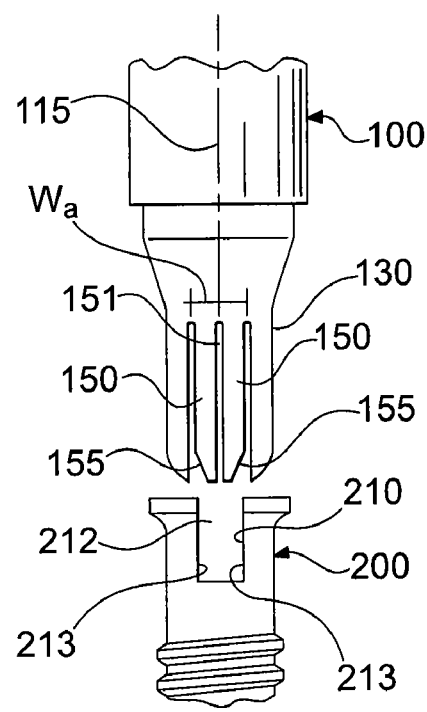
FIG. 11 is another perspective view of the surgical tool and fastener shown in FIG. 1.
Figure 12:
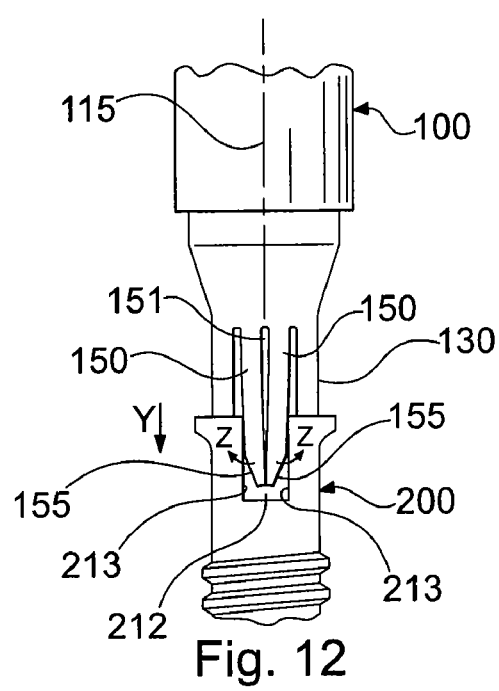
FIG. 12 is another perspective view of the surgical tool and fastener shown in FIG. 1.

Referring now to FIGS. 11 and 12, a manner of operating surgical driver 100 will be described. Driver 100 is initially positioned above a fastener 200 with the longitudinal axis 115 of the driver coaxial (or substantially coaxial) with the axis of the fastener. Fastener engagement tip 130 is aligned with a Philips head slot 210 on fastener 200, with spring extensions 150 aligned parallel with a slot section 212 in the fastener, as shown in FIG. 11. Driver 100 is then advanced toward the fastener head in a direction represented by arrow Y in FIG. 12.

Initially, spring extensions 150 are in the first arrangement (relaxed state), having a combined width $W_a$ that exceeds the width of slot section 212. As driver 100 is advanced, the chamfered edges 155 engage sidewalls 213 of slot section 212. The tapered configuration provided by chamfered edges 155 cause reaction forces to be directed inwardly onto spring extensions 150, toward longitudinal axis 115 of driver. In response, spring extensions 150 deflect inwardly into slit 151. As a result, spring extensions 150 are compressed inwardly toward one another, decreasing the combined width of the spring extensions $W_a$ so that the spring extensions can pass further into slot section 212. Driver 100 is advanced in direction Y until fastener engagement tip 130 either bottoms out in fastener slot 200, or is otherwise stopped from further advancement by the relative dimensions and/or shape of the slot. FIG. 12 shows fastener engagement tip 130 fully inserted into slot section 212.

In the fully inserted position, spring extensions 150 are deflected out of their relaxed state, with stored energy. Under this stored energy, spring extensions are biased outwardly and away from one another so as to exert an outward force on side walls 213 of slot section 212. The direction of these outward forces are represented by arrows Z in FIG. 12. The outward biasing forces create a press fit condition around the spring extensions, enhancing the engagement between fastener engagement tip 130 and fastener 200. The amount of force needed to pull the fastener engagement tip 130 out of the fastener 200 (or "pull-out force") is much greater than the threshold pull-out force needed to remove a conventional Philips head driver inserted in the same slot. As a result, the likelihood of the fastener falling off the driver tip, or being knocked off the driver tip, is greatly reduced.

Figure 5:
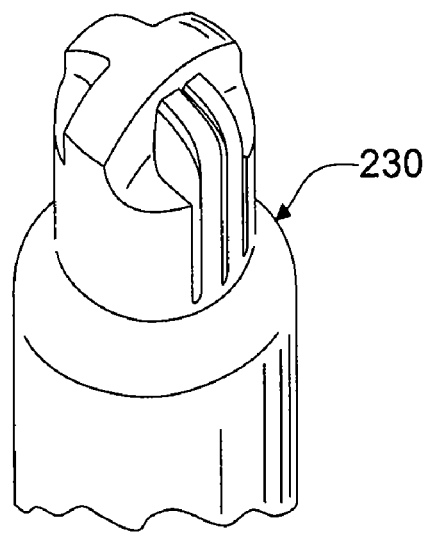
FIG. 5 is a perspective view of another fastener engagement tip in accordance with the invention, truncated for clarity.
Figure 6:
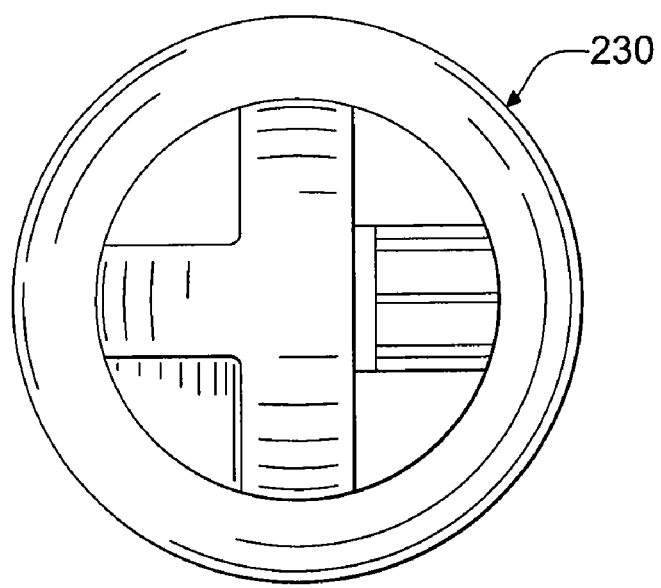
FIG. 6 is an end view of the fastener engagement tip of FIG. 5.

Fastener engagement tips in accordance with the invention may have a hollow passage to accommodate guidewires or other components. Referring again to FIGS. 3 and 4, fastener engagement tip 130 has a hollow bore 136 extending from the coupling end 132 of the fastener engagement tip to engagement end 134. A hollow passage is entirely optional. FIGS. 5 and 6 show another fastener engagement tip 230 in accordance with the invention having a solid center section.

As noted above, fastener engagement tips in accordance with the present invention can be embodied in a number of conventional screw driver configurations, and are not limited to Philips head tips. For example, fastener engagement tips in accordance with the present invention can be embodied in slotted (or "flat") head tips, square head tips, hexagonal head tips, hexalobular (or "star") head tips, or spline head tips, to name a few examples.

Referring now to FIGS. 7-10, fastener engagement tips in accordance with other embodiments of the invention are shown, each having a unique configuration to accommodate a specific screw slot configuration. For the most part, the fastener engagement tips in FIGS. 7-10 operate under the same general principles as the Philips head configurations of FIGS. 1-6. For example, the fastener engagement tips shown in FIGS. 7-10 utilize one or more spring extensions. In addition, the fastener engagement tips shown in FIGS. 7-10 may be integrally formed with shanks and handles, forming a one-piece driver. Alternatively, the fastener engagement tips shown in FIGS. 7-10 may be separate components that are either permanently attached to shanks, or detachably coupled to shanks. Therefore, many features of the fastener engagement tips in FIGS. 7-10 will not be described, with the understanding that many of their features are identical to or analogous with features shown in FIGS. 1-6. FIGS. 1-10 are intended to be viewed collectively so as to depict and encompass various embodiments that combine features from any combination of Figures.

Figure 7:
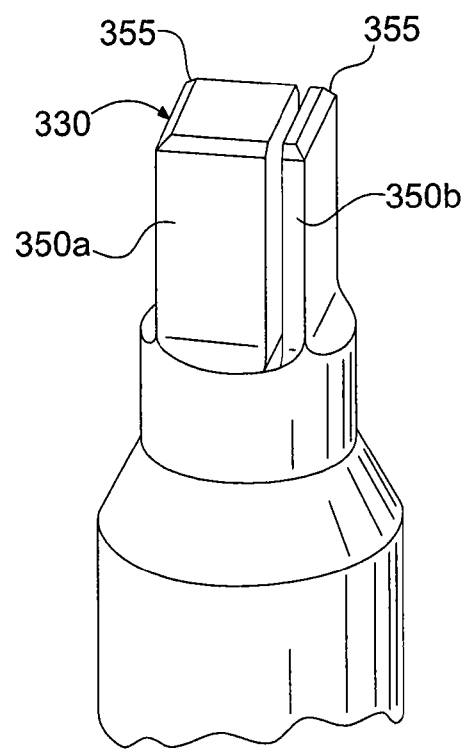
FIG. 7 is a perspective view of another fastener engagement tip in accordance is with the invention, truncated for clarity.

FIG. 7 shows a fastener engagement tip 330 having a square head configured to engage a square fastener slot. Fastener engagement tip 330 includes a wider extension 350a and a narrower extension 350b, each being shown in a relaxed state. Extensions 350a, 350b can deflect toward one another into a deflected state, each storing energy. Alternatively, extension 350a may be substantially rigid, and extension 350b may be flexible. As with other embodiments, extensions 350a, 350b each include a chamfered or beveled edge 355 to facilitate insertion of the extensions into a screw slot.

Figure 8:
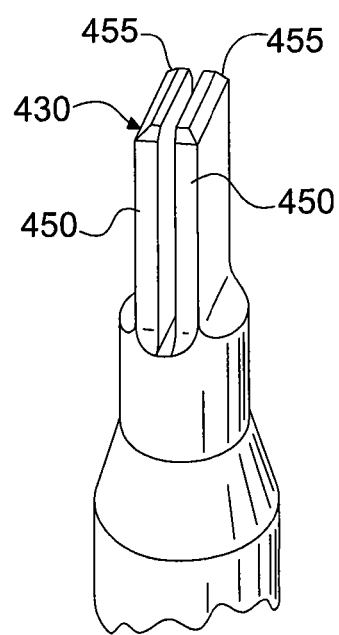
FIG. 8 is a perspective view of another fastener engagement tip in accordance with the invention, truncated for clarity.

FIG. 8 shows another fastener engagement tip 430 having a flat head configuration for engaging a flat head fastener slot. Fastener engagement tip 430 includes a pair of narrow-width spring extensions 450 that collectively form a flat head tip. Extensions 450 can deflect toward one another and toward the longitudinal axis of the fastener engagement tip, into a deflected state under stored energy. As with other embodiments, spring extensions 450 each include a chamfered or beveled edge 455 to facilitate insertion of the extensions into a screw slot.

Figure 9:
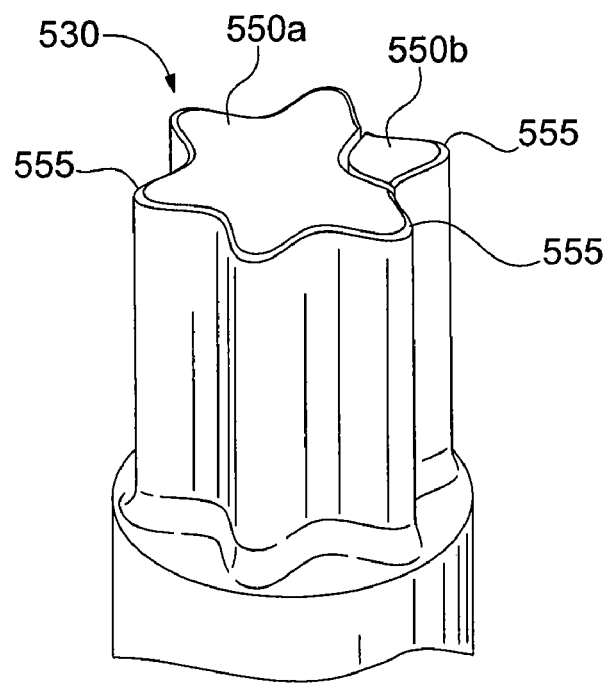
FIG. 9 is a perspective view of another fastener engagement tip in accordance with the invention, truncated for clarity.

FIG. 9 shows another fastener engagement tip 530 having a hexalobular (or "star") head configuration for engaging a star head fastener slot. Fastener engagement tip 530 includes a main extension 550a and a spring extension 550b that collectively form a star head tip. Extensions 550a, 550b can deflect toward one another and into a deflected state under stored energy. As with other embodiments, extensions 550a, 550b each include a chamfered or beveled edge 555 to facilitate insertion of the extensions into a screw slot.

Figure 10:
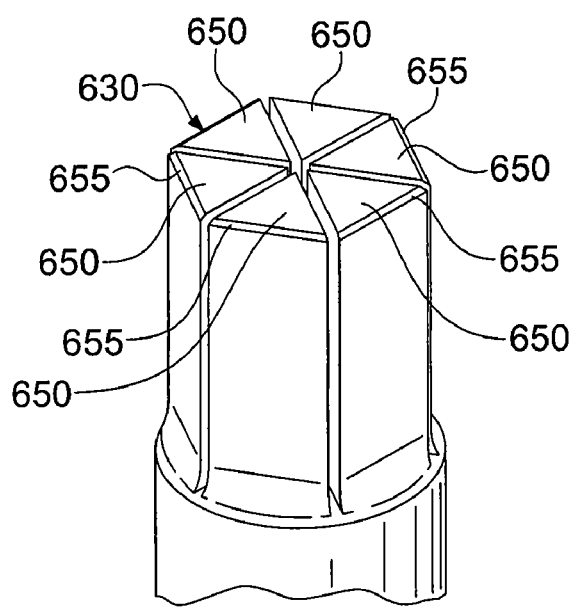
FIG. 10 is a perspective view of another fastener engagement tip in accordance with the invention, truncated for clarity.

FIG. 10 shows another fastener engagement tip 630 having a hexagonal head configuration for engaging a hexagonal head fastener slot. Fastener engagement tip 630 includes six triangular spring extensions 650 that collectively form a hexagonal head tip. Extensions 650 can deflect toward one another and toward the longitudinal axis of the fastener engagement tip, into a deflected state under stored energy. As with other embodiments, spring extensions 650 each include a chamfered or beveled edge 655 to facilitate insertion of the extensions into a screw slot.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A surgical tool for driving a fastener into bone, the surgical tool comprising a proximal end, a distal end and a longitudinal axis extending from the proximal end to the distal end, the surgical tool comprising a fastener engagement tip having at least two extensions for insertion into a slot in a head of a fastener, the at least two extensions extending substantially parallel to one another in a direction substantially parallel to the longitudinal axis of the surgical tool, at least one of the at least two extensions being resiliently flexible and deflectable between a first arrangement, in which it is in a relaxed state, and a second arrangement, in which it is deflected toward the other of the at least two extensions, the at least two extensions compressed together in the second arrangement so that the at least two extensions fit inside a slot in a head of a fastener, the fastener engagement tip forming a Philips head screw driver tip having four blades, with at least one of the four blades comprising the at least two extensions.

2. The surgical tool of claim 1 comprising a handle at the proximal end and a shaft connecting the handle with the fastener engagement tip.

3. The surgical tool of claim 2, wherein the fastener engagement tip is detachably connected to the shaft.

4. The surgical tool of claim 2, wherein the shaft comprises a socket, and the fastener engagement tip is detachably connected to the shaft in the socket.

5. The surgical tool of claim 1, wherein at least one of the at least two extensions comprises a chamfered edge.

6. The surgical tool of claim 1, wherein the fastener engagement tip comprises a Philips screwdriver head.

7. The surgical tool of claim 1, wherein each of the at least two extensions comprises an inward facing edge and an opposing outward facing edge, the inward facing edge of one of the at least two extensions facing the inward facing edge of the other of the at least two extensions, the outward facing edges each comprising a beveled face, the beveled faces converging toward one another as they extend toward the distal end of the surgical tool.

8. The surgical tool of claim 1, wherein the at least two extensions are at least two spring extensions.

9. The surgical tool of claim 8, wherein when the at least two spring extensions are in the second arrangement, at least one of the at least two spring extensions is deflected into a condition under a stored energy, said stored energy biasing said at least one of the at least two spring extensions toward the first arrangement.

10. The surgical tool of claim 9 comprising a handle at the proximal end and a shaft connecting the handle with the fastener engagement tip.

11. The surgical tool of claim 10, wherein the fastener engagement tip is detachably connected to the shaft.

12. The surgical tool of claim 10, wherein the shaft comprises a socket, and the fastener engagement tip is detachably connected to the shaft in the socket.

13. The surgical tool of claim 9, wherein at least one of the at least two spring extensions comprises a chamfered edge.

14. The surgical tool of claim 9, wherein the stored energy is sufficient to create a press fit connection around the at least two spring extensions when the at least two spring extensions are inserted in a slot in a fastener head.

15. The surgical tool of claim 1, wherein the four blades comprise a first blade, a second blade, a third blade and a fourth blade, the first blade comprising the at least two extensions, and the second, third and fourth blades each being solid blades.

16. The surgical tool of claim 15, wherein the first blade has a blade width $W_a$ when the extensions are in the first arrangement, and the second, third and fourth blades each have a blade width $W_b$, wherein $W_a$ is greater than $W_b$.

* * * * *